United States Patent [19]

Christensen et al.

[11] 4,264,621
[45] Apr. 28, 1981

[54] 5-SUBSTITUTED-3-(2-AMINOETHYLTHIO)-6-(1-HYDROXYETHYL)-7-OXO-1-AZABICYCLO[3.2.0]HEPT-2-ENE-2-CARBOXYLIC ACID

[75] Inventors: Burton G. Christensen, Scotch Plains; David B. R. Johnston, Warren; Susan M. Schmitt, Scotch Plains, all of N.J.

[73] Assignee: Merck & Co., Inc., Rahway, N.J.

[21] Appl. No.: 60,551

[22] Filed: Jul. 25, 1979

[51] Int. Cl.³ .................... C07D 487/04; A01K 31/40
[52] U.S. Cl. ................ 424/274; 260/239 A; 260/245.2 T; 542/416; 544/90
[58] Field of Search .................. 260/245.2 T; 424/274

[56] References Cited

U.S. PATENT DOCUMENTS

| | | | |
|---|---|---|---|
| 3,950,357 | 4/1976 | Kahan et al. | 260/245.2 T |
| 4,153,714 | 5/1979 | Ponsford | 424/274 |

OTHER PUBLICATIONS

Johnston et al., Heterocycles, vol. 9, No. 6, p. 791, (1978).

*Primary Examiner*—Mary C. Lee
*Attorney, Agent, or Firm*—Frank M. Mahon; James A. Arno; Julian S. Levitt

[57] ABSTRACT

Antibiotic 5-substituted-3-(2-aminoethylthio)-6-(1-hydroxyethyl)-7-oxo-1-azabicyclo[3.2.0]hept-2-ene-2-carboxylic acids (I) are disclosed:

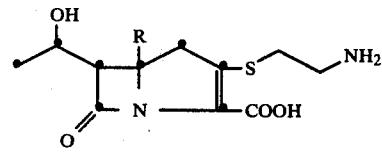

wherein R is alkyl, cycloalkyl, cycloalkylalkyl, aryl, aralkyl or heteroaryl.

4 Claims, No Drawings

5-SUBSTITUTED-3-(2-AMINOETHYLTHIO)-6-(1-HYDROXYETHYL)-7-OXO-1-AZABICYCLO[3.2.0-]HEPT-2-ENE-2-CARBOXYLIC ACID

BACKGROUND OF THE INVENTION

This invention relates to antibiotic 5-substituted-3-(2-aminoethylthio)-6-(1-hydroxyethyl)-7-oxo-1-azabicyclo(3.2.0)hept-2-ene-2-carboxylic acids (I):

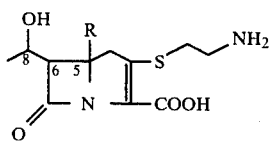

Wherein R is substituted or unsubstituted: alkyl having 1-6 carbon atoms, trifluoromethyl, phenyl, phenylalkyl having 7-12 carbon atoms, cycloalkyl having 3-6 carbon atoms, cycloalkylalkyl having 3-6 ring carbon atoms, and 1-6 carbon atoms in the alkyl moiety, and heteroaryl having 4-6 atoms in the ring, one or more of which is selected from O, N or S; and wherein the substituent or substituents on the foregoing radicals are selected from: OH, COOH, Cl, F, Br, $NH_2$, alkyl and alkoxyl having 1-3 carbon atoms.

This invention also relates to the pharmaceutically acceptable salt and ester derivatives of I; pharmaceutical compositions comprising I and such derivatives; and to methods of treatment comprising administering such compounds and compositions when an antibiotic effect is indicated.

There is a continuing need for new antibiotics, for unfortunately there is no static effectiveness of a given antibiotic because continued wide scale usage of any such antibiotic selectively gives rise to resistant strains of pathogens. In addition, the known antibiotics suffer from the disadvantage of being effective only against certain types of microorganisms. Accordingly, the search for new antibiotics continues.

Unexpectedly, it has been found that the compounds of the present invention are broad spectrum antibiotics, which are useful in animal and human therapy and in inanimate systems.

Thus, it is an object of the present invention to provide a novel class of antibiotics which are 5-substituted analogues of the antibiotic thienamycin. These antibiotics are active against a broad range of pathogens which representatively include both gram positive bacteria such as S. aureus, Strep. pyogenes and B. subtilis and gram negative bacteria such as E. coli, Proteus morganii, Serratia, Pseudomonas and Klebsiella. Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

The compounds of the present invention (I, above) are conveniently prepared by the following scheme:

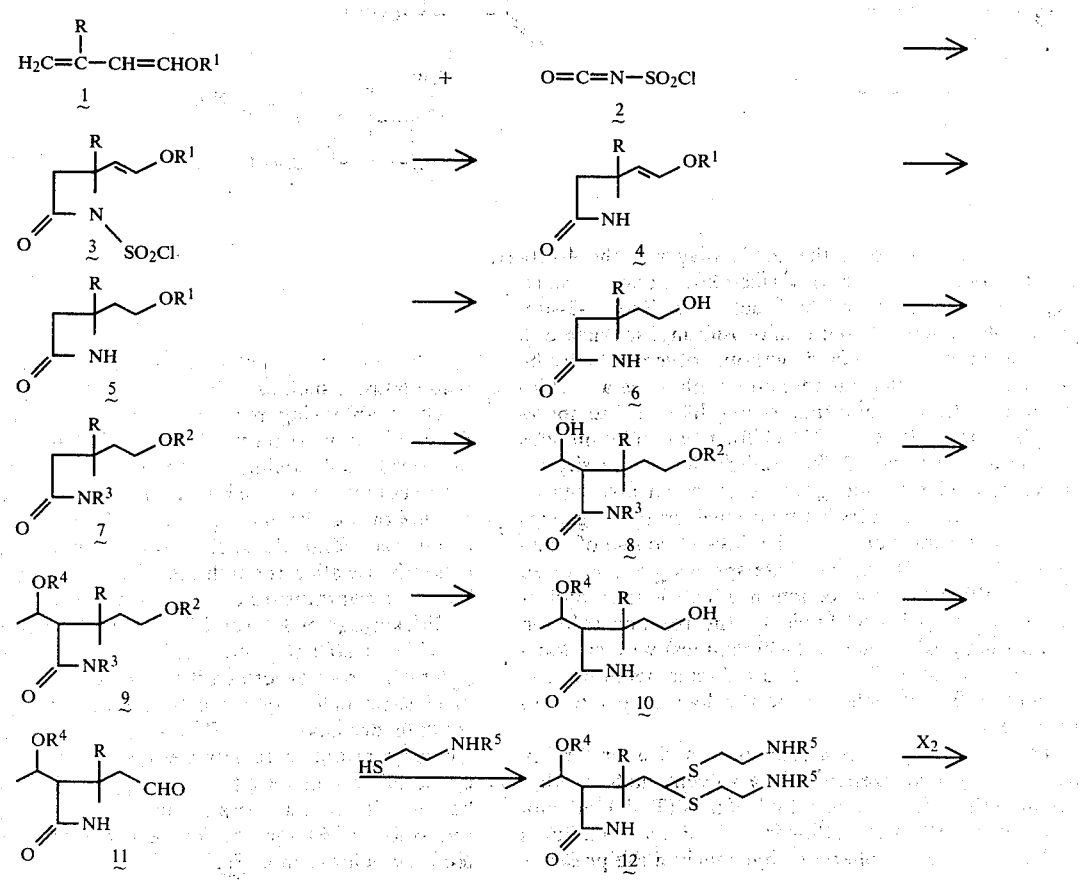

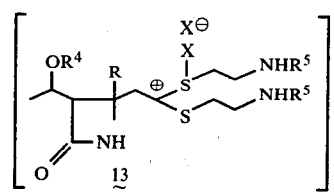
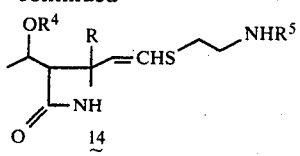
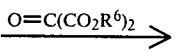
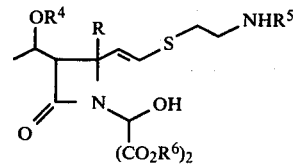
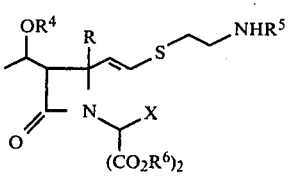
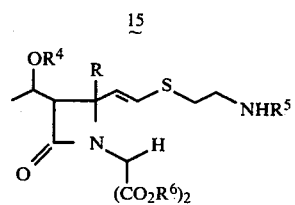
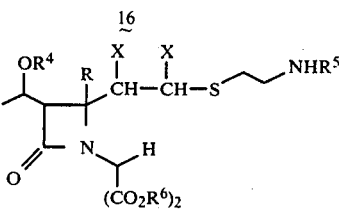
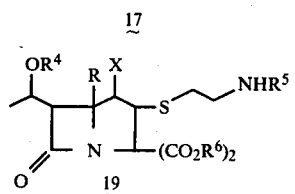
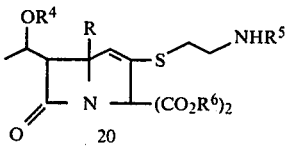
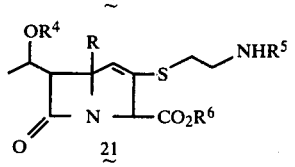
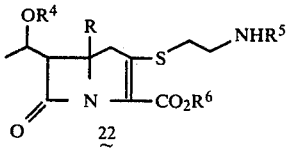
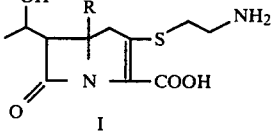

In words relative to the above diagram, the 4-substituted-4-(2-substituted-vinyl)azetidine-2-one, $\underline{4}$, starting material is prepared by reacting an $R^1$-oxy-3-substituted-butadiene, $\underline{1}$, with chlorosulfonylisocyanate $\underline{2}$. The reaction is conducted without solvent or may be run in solvent such as diethyl ether, ethyl acetate, chloroform, methylene chloride, or the like, at a temperature of from $-78°$ C. to $25°$ C. for from a few minutes to 1 hour to provide $\underline{3}$. The radical $R^1$ is an easily removable acyl blocking group such as an alkanoyl or aralkanoyl which bears no functional group or groups which might interfere with the desired course of reaction ($\underline{1}+\underline{2}\rightarrow\underline{3}\rightarrow\underline{4}$). Intermediate species $\underline{3}$ is converted to the sulfinamide by reduction which is then hydrolyzed to $\underline{4}$ at pH 6-8. Typically the reaction solution comprising $\underline{3}$ is contacted (5-30 minutes) with an aqueous solution (at $0°-25°$ C.) of a reducing agent such as sodium sulfite, thiophenol, or the like, at pH 6-8 to provide $\underline{4}$.

The reaction $\underline{4}\rightarrow\underline{5}$ is a reduction, and is preferably achieved by hydrogenation in a solvent such as ethyl acetate ether, dioxane, tetrahydrofuran (THF), ethanol or the like at $0°$ to $25°$ C. for from 5 minutes to 2 hours under 1 to 10 atmospheres of hydrogen in the presence of a hydrogenation catalyst such as platinum metal or oxide thereof such as 10% Pd/C or the like.

The de-blocking reaction $\underline{5}\rightarrow\underline{6}$ is usually desirable when $R^1$ is acyl to permit the later alkylation, $\underline{7}\rightarrow\underline{8}$. The preferred de-blocking procedure is by alcoholysis wherein the solvent is a lower alkanol such as methanol, ethanol or the like in the presence of the corresponding alkali metal alkoxide, such as sodium methoxide. Typically, the reaction is conducted for from 5 minutes to 1 hour at a temperature of from $-10°$ to $25°$ C.

Blocking groups $R^3$ and $R^2$ are established ($\underline{6}\rightarrow\underline{7}$) to provide a suitably protected species for alkylation ($\underline{7}\rightarrow\underline{8}$). There is no criticality in the choice of blocking groups, provided only that they do not interfere with the intended alkylation. $R^3$ may be hydrogen, a triorganosilyl group such as trimethylsilyl or the like, or a cyclic ether such as 2-tetrahydropyranyl; $R^2$ may also be a cyclic ether such as 2-tetrahydropyranyl; alternatively $R^3$ and $R^2$ may be joined together to form protected species such as $\underline{7a}$:

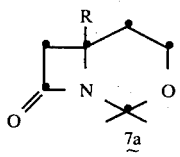

7a

For example, species such as 7a are conveniently prepared by treating 6 with 2,2-dimethoxypropane in the presence of a catalyst such as boron trifluoride etherate, toluene sulphonic acid, or the like in a solvent such as methylene chloride, ether, chloroform, dioxane or the like at a temperature of from −10° C. to 35° C. for from a few minutes to 1 hour.

The alkylation (7→8) is preferably conducted by treating 7 with a strong base such as lithium diisopropylamide, sodium amide, potassium hydride or the like in a solvent such as THF, glyme, ether, dimethylformamide (DMF), dimethylsulfoxide (DMSO) or the like at a temperature of from −78° C. to 0° C. The resulting anion is then treated with excess acetaldehyde to provide 8.

The reaction 8→9 establishes the blocking group $R^4$ and is typically accomplished by treating 8 with a base such as an alkali metal hydroxide, lithium diisopropylamide, 4-dimethylaminopyridine, or n-butyllithium in a solvent such as ether, THF, dioxane, DMF, DMSO or the like, followed by treatment with an acyl halide of choice such as alkanoyl, aralkanoyl or nuclear substituted aralkanoyl, or alkyl, aryl or aralkyl, substituted aralkyl or substituted aryl haloformate such as p-nitrobenzylchloroformate, o-nitrobenzylchloroformate, or the like, at a temperature of from −78° C. to 25° C. for from 1-24 hours.

The de-blocking reaction 9→10 is typically conducted by acid hydrolysis such as aqueous acetic acid at a temperature of from 25° C. to 75° C. for from 5 minutes to 3 hours.

The aldehyde intermediate 11 is prepared by treating 10 with an oxidizing agent such as CrO₃.2(pyridine) in CH₃CN, 1:1 mixture of dimethylsulfoxide and acetic anhydride, cyclohexylcarbodiimide in DMSO or the like at a temperature of from 0°–25° C. for from 5 minutes to 1 hour. The resulting species 11 in a solvent such as acetonitrile, methylene chloride, chloroform or the like at a temperature of from −10° to 25° C. is treated with an excess of N-blocked cysteamine, HSCH₂—CH₂NHR⁵, in the presence of an acid catalyst such as boron trifluoride etherate, toluene sulphonic acid or the like to provide 12. Typically, the reaction requires from 1 to 60 minutes.

There is no criticality as to the identity of the N-protecting group, $R^5$, or the cysteamine reagent and suitable groups are p-nitrobenzyloxycarbonyl, o-nitrobenzyloxycarbonyl, t-butyloxycarbonyl, 2,2,2-trichloroethoxycarbonyl, phthaloyl, or the like.

The vinyl sulphide 14 is obtained via intermediate 13 by treating 12 with a halogen such as chlorine or bromine (X=Cl or Br) in a solvent such as ether, methylene chloride, tetrahydrofuran, glyme or the like at a temperature of from −78° to 30° C. for from 1 to 30 minutes, followed immediately by treating with an olefin such as cyclohexene, isobutylene, or the like in the presence of base such as triethylamine, DBU, sodium hydride, or the like in a solvent such as DMF, glyme, THF, HMPA. The solution is held at −20° to 25° C. for from 1 to 8 hours to yield 14.

The vinyl sulphide species 14 is reacted with a diester of oxomalonic acid (or its monohydrate) to provide 15. There is no criticality as to the identity of the ester moiety, $R^6$, of the oxomalonic acid. $R^6$ may be a conventional, easily removable blocking group or it may be a pharmaceutically acceptable ester moiety. Suitable ester radicals $R^6$ are p-nitrobenzyl, benzyl, o-nitrobenzyl, t-butyl, 2,2,2-trichloroethyl. The reaction 14→15 is typically conducted in a high boiling organic solvent such as benzene, toluene, cyclohexane, halo aromatic or the like at a temperature of from about 50° C. to reflux for from 0.5 to 6 hours.

The halogenation reaction 15→16 is typically conducted in a solvent such as THF, glyme, ether, methylene chloride, chloroform or the like in the presence of a halogenating agent such as thionyl chloride, phosphorous pentachloride or the like in the presence of base such as pyridine at a temperature of from −20° to 25° C. for from 5 minutes to 3 hours. The selective reduction of 15→17 via 16 is completed by treating 16 with tributylphosphine, triphenylphosphine or the like in aqueous DMF or similar aqueous systems involving dioxane, THF, glyme, DMSO, or acetone in the presence of K₂HPO₄ at a temperature of from about 0°–50° C. for from 10 minutes to 5 hours.

Species 17 is halogenated by the previous procedure (12→13), but omitting the addition of the cyclohexene or other olefin, to provide the dihalo species 18. Species 18 is treated with a base such as triethylamine, sodium hydride or potassium hydride in a solvent such as DMF, acetonitrile, methylene chloride, chloroform, glyme or the like at a temperature of from about −78° to 25° C. for 1 to 5 hours to provide 19. Species 19 is converted to 20 on treatment with a strong base such as 1,5-diazabicyclo[5.4.0]undec-5-ene (DBU), 1,5-diazabicyclo[3.4.0]non-5-ene(DBN), or the like in a solvent such as DMSO, acetone, chloroform, DMF, THF, glyme or the like or on treatment with AgF in pyridine at a temperature of from 0°–40° C. for from ¼ to 24 hours. The reaction 20→21 is conducted by treating 20 with an aromatic base such as pyridine, s-collidine or lutidine, in the presence of a displacing agent such as lithium iodide, lithium bromide, sodium bromide, or the like at a temperature of from about 80°–150° C. for from 15 minutes to 2 hours. An aqueous work up of the resulting reaction mixture provides 21. Isomerization of the double bond 21→22 is accomplished by treating 21 in a solvent such as DMF, DMSO, ethyl ether, THF, glyme, methylene chloride with a strong base such as diisopropylamine, DBU, DBN, or the like at a temperature of from 0° to about 25° C. for from a few minutes to 2 hours or until equilibrium has been established as determined by examination of sample aliquots by ultraviolet absorption or by thin layer chromatography. The final reaction 22→I (by hydrogenolysis of the blocking groups) is accomplished by treating 22 in a solvent such as dioxane, ethanol, THF or the like or an aqueous mixture thereof in the presence of a Platinum metal catalyst such as Pd/C under a hydrogen pressure of from 1-4 atmospheres for from 0.5 to 8 hours at a temperature of from about 0°–25° C.

The above-described total synthesis may also advantageously start with a 4-substituted-4-vinyl azetidinone (23), below rather than the enol acylate azetidinone (4, above). The following scheme illustrates this 4-substituted-4-vinyl-azetidinone embodiment of the present invention; notice that it ties into the above scheme at species 14.

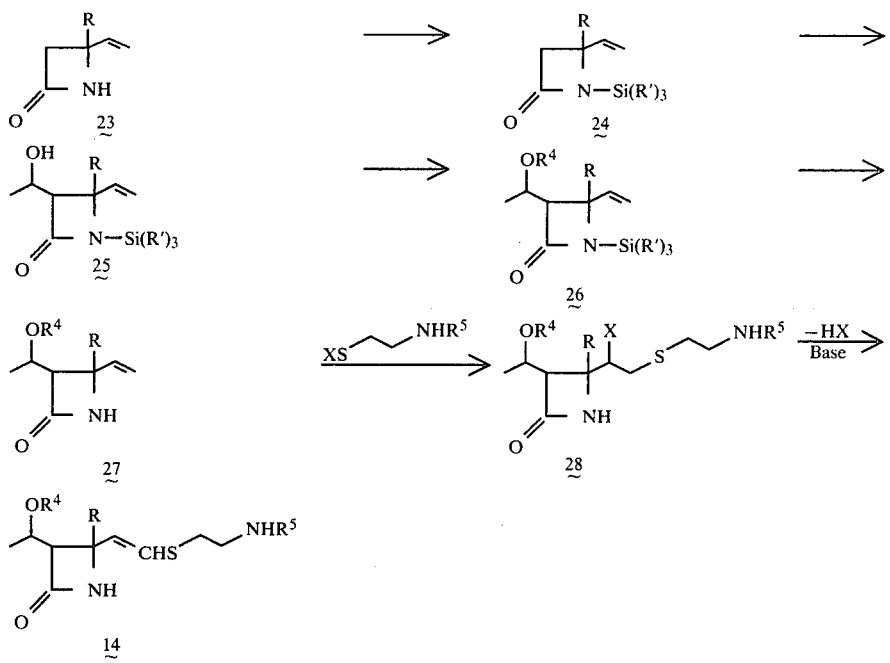

In words relative to the above reaction diagram, the 4-substituted-4-vinyl azetidinone 23 is silylated to provide the N-silyl species 24. The groups R' on the silyl radical are loweralkyl having from 1–6 carbon atoms especially preferred triorganosilyl groups are trimethylsilyl and t-butyl-dimethylsilyl. Typically the silylation (23→24) is achieved by treating 23 in a solvent such as DMF, DMSO, HMPA or the like with the silylating agent of choice, dimethyl t-butylsilyl chloride, and a base such as Et₃N, pyridine, N,N-dimethylaniline and the like at a temperature of from −10° to 30° C. for from 1 to 8 hours. Species 24 is alkylated to form 25 by treatment with acetaldehyde in the presence of base. This reaction 24→25 is conducted exactly as described above for the alkylation 7→8. The O-protecting group is established in the reaction 25→26. The protecting group $R^4$ is as previously defined and the reaction 25→26 is exactly analogous to the above described reaction 8→9. The removal of the N-triorganosilyl group is accomplished in reaction 26→27 by mild acid catalyzed solvolysis. The halo sulfide species 28 is obtained from 27 by treating 27 in a solvent such as methylene chloride, THF, glyme, or the like with the reagent $XSCH_2CH_2NHR^5$ wherein $R^5$ has previously been defined and X is halogen such as chloro or bromo at a temperature of from −50° C. to 50° C. for from 1 to 16 hours. The final sulfide intermediate 14, which is common to the above illustrated scheme of total synthesis is obtained from 28 by elimination of HX on treatment of 28 with a base such as 1,5-diazabicyclo (5.4.0)undec-5-ene (DBU), 1,5-diazabicyclo[4.3.0]non-5-ene, (DBN), 1,4-diazabicyclo[2.2.2]octane, (DABCO), or silver fluoride in a solvent such as DMSO, pyridine, DMF, HMPA or the like at a temperature of from −20° to 50° C. for from ¼ to 16 hours.

The products of this invention (I) form a wide variety of pharmacologically acceptable salts with inorganic and organic bases; these include, for example, metal salts derived from alkali or alkaline earth metal hydroxides, carbonates or bicarbonates and salts derived from primary, secondary or tertiary amines such as monoalkylamines, dialkylamines, trialkylamines, loweralkanolamines, di-loweralkanolamines, lower alkylenediamines, N,N-diaralkyl lower alkylenediamines, aralkylamines, amino substituted lower alkanols, N,N-di-lower alkylamino substituted lower alkanols, amino-, polyamino- and guanidino-substituted lower alkanoic acids and nitrogen-containing heterocyclic amines. Representative examples include salts derived from sodium hydroxide, sodium carbonate, sodium bicarbonate, potassium carbonate, potassium hydroxide, calcium carbonate, trimethylamine, triethylamine, piperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline, N-methylglucamine and the like. Acid addition salts, e.g., with hydrochloric, tartaric, hydrobromic, sulfuric nitric, toluene-p-sulphonic and methane sulphonic acids may also be employed.

The salts can be mono-salts such as the monosodium salt obtained by treating one equivalent of sodium hydroxide with one equivalent of the product (I), also mixed di-salts. Such salts may be obtained by treating one equivalent of a base having a divalent cation, such as calcium hydroxide, with one equivalent of the product (I). The salts of this invention are pharmacologically acceptable non-toxic derivatives which can be used as the active ingredient in suitable unit-dosage pharmaceutical forms. Also, they may be combined with other drugs to provide compositions having a broad spectrum of activity.

The compounds of the present invention are valuable antimicrobial substances which are active against various gram-positive and gram-negative pathogens. Thus the free acid, free base, and especially the salts thereof such as amine and metal salts, particularly the alkali metal and alkaline earth metal salts, are useful bactericides and can be used for removing susceptible pathogens from dental and medical equipment, for separating microorganisms, and for therapeutic use in humans and animals. For this latter purpose pharmacologically acceptable salts with inorganic and organic bases such as those known in the art and used for the administration of penicillins and cephalosporins can be utilized. For example, salts such as alkali metal and alkaline earth metal salts, and primary, secondary and tertiary amine salts can be used for this purpose. These salts can be combined with pharmaceutically acceptable liquid and solid vehicles to form suitable dosage unit forms such as pills, tablets, capsules suppositories, syrups, elixirs and the like which can be prepared in accordance with procedures well known in this art.

The novel compounds are valuable antibiotics active against various gram-positive and gram-negative bacteria, and accordingly, find utility in human and veterinary medicine. The compounds of this invention can therefore be used as antibacterial drugs for treating infections caused by gram-positive or gram-negative bacteria, for example against *Staphylococcus aureus, Escherichia coli, Klebsiella pneumoniae, Bacillus subtilis, Salmonella typhosa,* Pseudomonas and *Bacterium proteus.* The antibacterials of the invention may further be utilized as additives to animal feedingstuffs, for preserving foodstuffs and disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial application, for example in waterbased paints and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preparably presented in a form suitable for absorption by the gastro-intestinal tract. Tablets and capsules for oral administration may be in unit dose presentation form, and may contain conventional excipients such as binding agents, for example syrup, acacia, gelatin, sorbitol, tragacanth, or polyvinylpyrrolidone; fillers for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g., cocoa butter of other glyceride.

Compositions for injection may be presented in unit dose form in ampules, or in multidose containers with an added perservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder or liquids sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of adminstration, the parenteral route being preferred for generalized infections and the oral route for intestinal infections. In general, a daily oral dosage consists of from about 5 to about 600 mg. of active ingredient per kg. of body weight of the subject in one or more applications per day. A preferred daily dosage for adult humans lies in the range of from about 15 to 240 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10-60%. The compositions will generally contain from about 15 mg. to about 1500 mg. of the active ingredient; however, in general, it is preferable to employ a dosage amount in the range of from about 250 mg. of 1000 mg. In parenteral administration the unit dosage is usually the pure compound in a slightly acidified sterile water solution or in the form of a soluble powder intended for solution.

The following examples, illustrate but do not limit the product, process, compositional or method of treatment aspects of the present invention.

EXAMPLE 1

Preparation of 4-(2-acetoxyvinyl)-4-methyl-azetidine-2-one

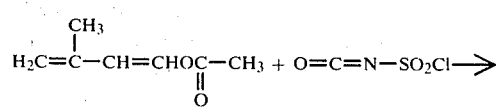

-continued

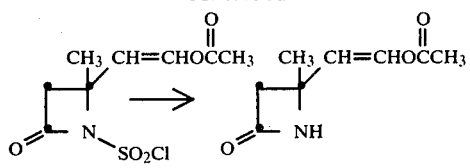

A solution of 1.0 ml distilled chlorosulfonylisocyanate (1.65 g; 11.7 mmoles) in 2.5 ml anhydrous diethyl ether is cooled under $N_2$ in a $-20°$ C. bath.

A solution of 1-acetoxy-3-methyl-butadiene (22 mmoles) in 2.5 ml anhydrous ether is similarly cooled under $N_2$ in a $-20°$ C. bath.

The chlorosulfonylisocyanate solution is added dropwise to the acetoxybutadiene solution by means of a Teflon tube immersed in the CSI solution and pressurized with $N_2$. The addition takes 10 minutes, and the reaction is stirred at $-20°$ C. for 0.5 hour.

A solution of 2 g sodium sulfite and 5 g $K_2HPO_4$ in 20 ml $H_2O$ is prepared during the above 0.5 hour reaction time and is cooled in an ice bath; 20 ml of ether is added and the mixture is vigorously stirred in an ice bath. At the end of the 30 minute reaction time, the reaction mixture is transferred, again using $N_2$ pressure and the Teflon tube, from the reaction flask which is maintained in the $-20°$ C. bath, to the vigorously stirred hydrolysis mixture. Rapid dropwise addition is completed in 5 minutes. The hydrolysis is allowed to continue for 5 additional minutes. The hydrolysis mix has a pH of 6–8, preferably pH 8.

The phases are separated, the ether phase is dried with $MgSO_4$. The aqueous phase is extracted three more times with 50 ml portions of ether, each being added to the initial ether/$MgSO_4$.

The dried extracts are filtered and concentrated under a $N_2$ stream to 5 ml.

A column of 10 g Baker silica gel, packed in ether is prepared, and the ether concentrate is applied to the top. Elution with ether affords the title compound.

EXAMPLE 2

Preparation of 4-(2-acetoxyethyl)-4-methyl-2-azetidinone

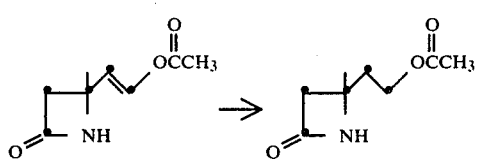

A solution of 4-(2-acetoxyvinyl)-4-methyl-2-azetidinone (10.0 g) 200 ml ethyl acetate containing 100 mg of 10% Pd/C is hydrogenated on a Parr shaker at 25° C. under 40 psi hydrogen for 15 minutes. The mixture is filtered through a bed of Supercel and washed with additional ethyl acetate. The combined filtrate is evaporated in vacuo to give 4-(2-acetoxyethyl)-4-methyl-2-azetidinone.

EXAMPLE 3

Preparation of 4-(2-hydroxyethyl)-4-methyl-2-azetidinone

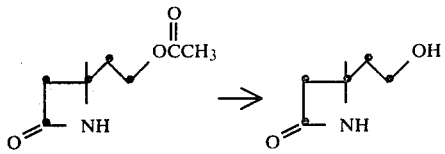

Under nitrogen at 0°, a solution of 4-(2-acetoxyethyl)-4-methyl-2-azetidinone (0.014 mole) in 25 ml anhydrous methanol is treated with a solution of sodium methoxide (77 mg, 1.4 mmoles) in 5 ml anhydrous methanol. After stirring for 1 hour, the solution is neutralized with glacial acetic acid. Removal of the methanol in vacuo gives crude 4-(2-hydroxyethyl)-4-methyl-2-azetidinone as an oil. The product is purified by chromatography on silica gel eluting with 10% MeOH/CHCl$_3$ to give the alcohol.

EXAMPLE 4

Preparation of 8-oxo-2,2,6-trimethyl-3-oxa-1-azabicylco[4.2.0]octane

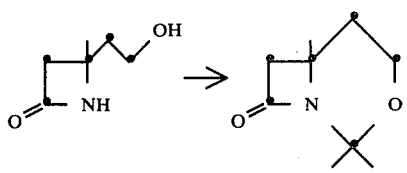

A solution of 4-(2-hydroxyethyl)-4-methyl-2-azetidinone (0.016 mole) and 2,2-dimethoxypropane (1.69 g, 0.016 mole) in 25 ml anhydrous methylene chloride is treated with boron trifluoride etherate (0.201 ml, 0.002 mole) at 25° C. The resulting solution is stirred for ten minutes. Removal of the solvent under reduced pressure gives an oil (2.5 g). Chromatography of the crude product on silica gel using 2:1 ethyl acetate/benzene as eluting solvent gives 8-oxo-2,2,6-trimethyl-3-oxa-1-azabicyclo[4.2.0]-octane.

EXAMPLE 5

Preparation of 8-Oxo-2,2,6-trimethyl-7-(1-hydroxyethyl)-3-oxa-1-azabicyclo[4.2.0]octane

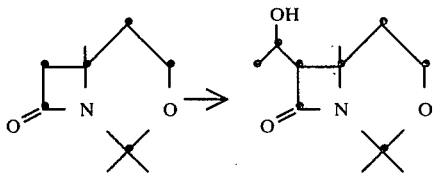

To a solution of 1.1 equivalents of freshly prepared lithium diisopropylamide in anhydrous tetrahydrofuran under a nitrogen atmosphere at $-78°$ is added a solution of 8-oxo-2,2,6-trimethyl- 3-oxa-1-azabicyclo[4.2.0]octane in anhydrous tetrahydrofuran which has been cooled to $-78°$ C. After two minutes, the resulting lithium enolate is treated with excess acetaldehyde. The solution is stirred for 30 minutes at $-78°$ and then poured into water. The aqueous phase is saturated with sodium chloride and extracted with ethyl acetate. The combined ethyl acetate solutions are dried over magnesium sulfate and filtered. The filtrate is evaporated under reduced pressure to give the crude product. Purification by chromatography on silica gel using ethylacetate/benzene gives 8-oxo-2,2,6-trimethyl-7-(1-hydroxyethyl)-3-oxa-1-azabicyclo[4.2.0]octane.

EXAMPLE 6

Preparation of 8-Oxo-2,2,6-trimethyl-7-(1-p-nitrobenzylcarbonyldioxyethyl)-3-oxa-1-azabicyclo[4.2.0]octane

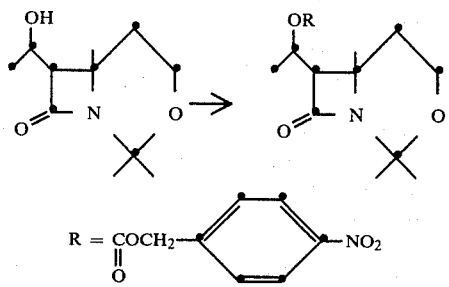

Under anhydrous conditions at 0° C. a solution of 8-oxo-2,2,6-trimethyl-7-(1-hydroxyethyl)-3-oxa-1-azabicyclo[4.2.0]octane (60 mg, 0.302 mmole) in 0.6 ml ether is treated with powdered potassium hydroxide (19 mg, 0.332 mmole). After a period of 15 minutes, p-nitrobenzylchloroformate (65 mg, 0.302 mmole) is added to the reaction mixture. Stirring is continued at 25° C. for an additional 15 hours. The mixture is partitioned between 1 M pH 7 phosphate buffer and more ether. The ether phase is washed with water and brine, dried over magnesium sulfate and filtered. Evaporation of the filtrate under reduced pressure and purification by preparative thick-layer chromatography on silica gel developing with 1:9 ethyl acetate/benzene gives 8-oxo-2,2,6-trimethyl-7-(1-p-nitrobenzylcarbonyldioxyethyl)-3-oxa-1-azabicyclo[4.2.0]octane.

EXAMPLE 7

Preparation of 3-(1-p-nitrobenzylcarbonyldioxyethyl)-4-(2-hydroxyethyl)-4-methyl-2-azetidinone

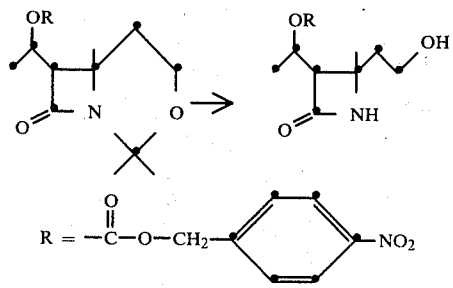

8-Oxo-3-oxa-2,2,6-trimethyl-7-(1-p-nitrobenzylcarbonyldioxyethyl)-1-azabicyclo[4.2.0]octane (1.0 g) is dissolved in 8 ml acetic acid and 2 ml water and heated at 65° C. for 1.25 hours. The acetic acid and water are removed under reduced pressure and the residue is taken up in benzene and evaporated to give 3-(1-p-nitrobenzylcarbonyldioxyethyl)-4-(2-hydroxyethyl)-4-methyl-2-azetidinone.

EXAMPLE 8

Preparation of 5-methyl-3-(2-aminoethylthio)-6-(1-hydroxyethyl)-7-oxo-1-azabicyclo[3.2.0]hept-2-ene-2-carboxylic acid

STEP A:

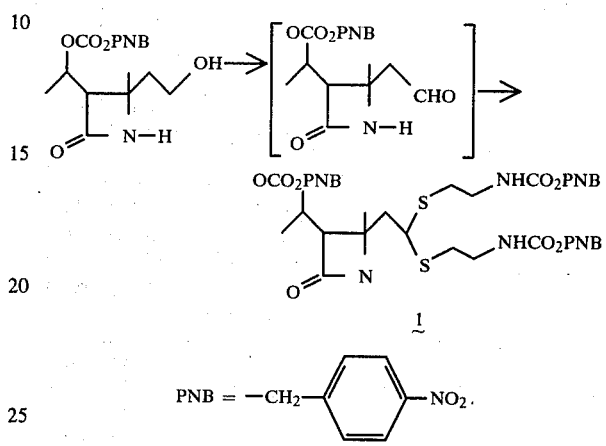

To 6.75 ml anhydrous pyridine (mw=79; ρ=0.982; 83.9 mmole) in 350 ml anhydrous acetonitrile is added 4.05 g anhydrous powdered chromium trioxide (mw=100; 40.5 mmole). After stirring at room temperature (25° C.) for 30 minutes, 9.6 g dried Supercell is added and stirring is continued for 5 additional minutes. A solution of 3-(1-p-nitrobenzylcarbonyldioxyethyl)-4-methyl-4-(2-hydroxyethyl)-2-azetidinone (9.5 mmole) in 30 ml anhydrous acetonitrile is added all at once. The reaction mixture is stirred under anhydrous conditions at room temperature (25° C.) for one hour. Addition of 9.6 g NaHSO₃ is followed by 5 minutes of stirring after which the reaction mixture is filtered through a mixed packed bed of 40 g silica gel and 40 g anhydrous magnesium sulfate. The bed is washed repeatedly with acetonitrile (total volume of filtrate ~600 ml). The filtrate is concentrated under a N₂ stream to 130 ml total volume. To this solution containing crude aldehyde at 0° C. under N₂ is added 9.64 g p-nitrobenzyloxycarbonylaminoethanethiol (mw=256; 37.7 mmole) as prepared below (Example 8, Step B). To the stirred reaction mixture is added 8.0 ml boron trifluoride etherate (mw=142; ρ=1.125; 63.4 mmole). After 1.5 hours at 0° C., the reaction mixture is poured into a stirred ice-cold mixture of 69 g K₂HPO₄-500 ml H₂O and 700 ml ethyl acetate (EA). The layers are separated and the aqueous one is saturated with NaCl and re-extracted with additional EA. The combination organic layers are washed twice with brine, dried over anhydrous MgSO₄ and filtered. The filtrate is concentrated under a N₂ stream and then pumped on high vacuum to give crude 1.

The material is chromatographed on 450 g silica gel (column height=48 cm; diameter=5.5 cm) packed and applied in CHCl₃ and eluted with increasing percentages of MeOH in CHCl₃ (0–4% MeOH/CHCl₃). Those fractions containing the desired product are combined, concentrated under N₂ stream; and pumped on high vacuum to give 1.

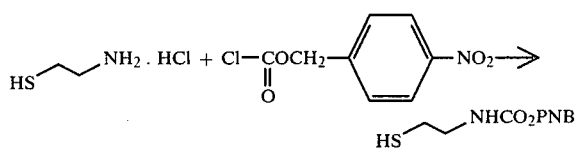

To 600 ml diethyl ether (Et₂O)-75 ml H₂O in an ice bath with stirring is added 3.2 g cysteamine hydrochloride (mw=114; 28.1 mmole). A solution of 7.14 g NaHCO₃ (mw=84; 85 mmole) in 75 ml H₂O is added. The ice bath is removed, and at room temperature a solution of 6.75 g p-nitrobenzylchloroformate (mw=216; 31.3 mmole) in 270 ml Et₂O is added dropwise over a period of one hour. After 10 additional minutes, the layers are separated. The ether layer is extracted with 150 ml 0.25 N HCl, and then with 200 ml brine. Each aqueous layer is then backwashed successively with 100 ml Et₂O. The combined Et₂O layers are dried over anhydrous MgSO₄, filtered, and concentrated under a N₂ stream. The crystalline residue is slurried in a small amount of ether, filtered, and the pale yellow crystals are dried under high vacuum to give 4.7 g p-nitrobenzyloxycarbonylaminoethanethiol (65% yield).

NMR (CDCl₃): 8.18 (d, J=8 Hz, aromatic protons ortho to nitro), 7.47 (d, J=8 Hz, aromatic protons meta to nitro), 5.27 (—N$\underline{H}$—), 5.20 (s, —C$\underline{H}_2$— φ-pNO₂), 3.40 (m, —C$\underline{H}_2$—NH—), 2.67 (m, —C$\underline{H}_2$—SH), 1.35 (t, J=8.5 Hz, —S$\underline{H}$) in ppm downfield from TMS.

IR (CHCl₃ solution) carbonyl- ~ 1725 cm⁻¹

M.S.-molecular ion-256, (M-47) at 209, (M-136) at 120, +CH₂φpNO₂ at 136.

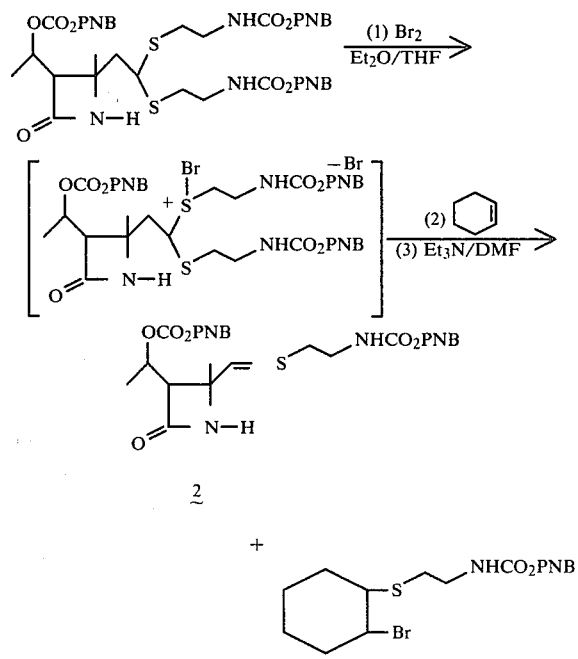

To 14.2 ml pentane (dried over 4A Linde molecular sieves) is added 0.5 ml Br₂ (mw=160; 9.75 mmole). To 6.02 mmole of $\underset{\sim}{1}$ in 58 ml tetrahydrofuran (THF) (freshly distilled from lithium aluminum hydride) (LAH) and 65 ml Et₂O (dried over 3A 1/16″ Linde molecular sieves) at 0° C. under N₂ with stirring is added dropwise 10 ml of the above 0.66 M Br₂ solution (6.6 mmole). After 10 minutes at 0° C., 0.67 ml cyclohexene (mw=82; ρ=0.81; 6.6 mmole) is added. After 5 minutes at 0° C., 1.7 ml triethylamine (mw=101; ρ=0.729; 12.3 mmole) is added immediately followed by 40 ml ice-cold dimethylformamide (DMF) (distilled from anhydrous CaSO₄ at 40 mm and stored over 4A Linde molecular sieves). The ice bath is removed, and stirring is continued for 2¼ hours at room temperature. The reaction mixture is poured into a stirred ice-cold mixture of 12.6 ml 1 M KH₂PO₄ 160 ml H₂O-500 ml (EA). After separation of the layers, the aqueous one is saturated with sodium chloride and re-extracted with EA. The combined organic layers are extracted once with brine, dried over anhydrous MgSO₄, filtered and concentrated under N₂ stream followed by pumping under high vacuum to provide crude $\underset{\sim}{2}$.

The material is chromatographed on 250 g silica gel (height=45 cm; diameter=4.5 cm) packed and applied in CHCl₃ and eluted with increasing percentages of MeOH in CHCl₃ (0–3% MeOH/CHCl₃). Those fractions containing clean product are combined, concentrated under a N₂ stream, and pumped on high vacuum to give $\underset{\sim}{2}$. Contaminated fractions are rechromatographed on silica gel using increasing percentages of EA in CHCl₃ (0–25% EA/CHCl₃) to give additional $\underset{\sim}{2}$.

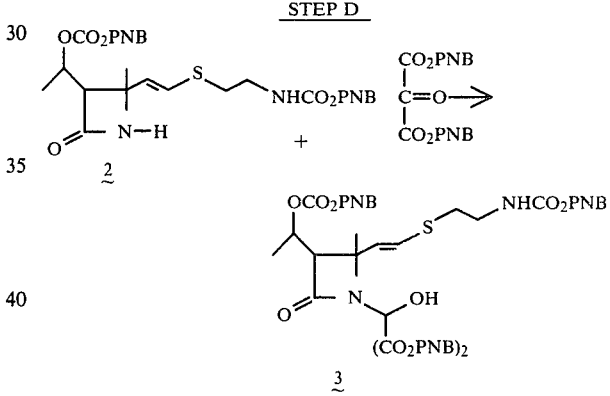

To a stirred solution of 2.48 g di(p-nitrobenzyl)-ketomalonate (from Example 8, Step E) (mw=388; 6.39 mmole) in 400 ml hot anhydrous toluene is added a solution of $\underset{\sim}{2}$ (4.39 mmole) in 20 ml THF (distilled from LAH) and 40 ml anhydrous toluene. After some of the solvent is boiled off, additional anhydrous toluene is added, and the azeodrying process is repeated three times. The solution is then refluxed under N₂ for 30 minutes. Additional toluene is then allowed to boil off yet the volume is not allowed to diminish to much that precipitation occurs. Total heating time is approximately 2½ hours. The clear yellow reaction mixture is removed from the oil bath and placed under a stream of N₂ which instantaneously causes clouding. After concentration, the residue is dissolved in CH₂Cl₂, dried over anhydrous MgSO₄, filtered, and concentrated under a N₂ stream to give crude $\underset{\sim}{3}$.

The material is chromatographed on 250 g silica gel packed and applied in CHCl₃ (height=43 cm; diameter=4.5 cm). Elution with 500 ml 0.5% MeOH/CHCl₃ is followed by continued elution with 1% MeOH/CHCl₃ for the remainder of the chromatography. After the emergence of excess reagent, those fractions containing pure 3 are combined, concentrated under a $N_2$ stream and then on high vacuum to give 3.

STEP E
Preparation of di-p-Nitrobenzyl ketomalonate

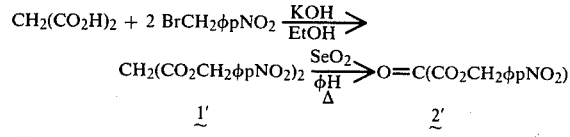

$\phi H$ = benzene

A mixture of 100 g p-nitrobenzyl bromide (0.46 mole), 28.6 g malonic acid (0.275 mole) and 750 ml ethanol (EtOH) is stirred and warmed on the steam bath until solution is achieved. A solution of 33 g KOH (>85% purity; ~0.6 mole) in 200 ml of water is added carefully with swirling. An additional 200 ml of water is added, and the two-phase system is refluxed for 1.8 hours. The lighter color homogeneous solution is cooled in ice for 1 hour and the crude product isolated by filtration, washed twice with a minimum of cold EtOH, and dried by pulling dry $N_2$ through the cake; 33.7 g of solid is obtained. If, during the refluxing stage the reaction mixture is slowly concentrated to ca. half volume by allowing refluxing solvent to distill off, the crude product yield rises to 77 g. The material is recrystallized from methanol to give pure di-p-nitrobenzyl malonate 1'.

A mixture of 23.4 g of 1', 10 g $SeO_2$, and 30–40 ml of xylene is stirred in a flask immersed in an oil bath. The bath temperature is raised over 1 hour to 130°14 135°. A gradual darkening of the reaction mixture is noted, and after a total of 4 hours at 130°–135°, most of the insoluble residue is black Se°. The mixture is cooled, $MgSO_4$ is added to remove the water, and Celite is added to aid in filtration. The mixture is filtered through Celite and the cake washed with xylene and a small portion of EtOAc. Final volume: 60 ml. A 100 g column of Baker Silica Gel is prepared in benzene and 10 ml of filtrate applied, then eluted with increasing amounts of EtOAc in benzene, 500 ml fractions being collected. After one 2% ethyl acetate (EtOAc)/$\phi H$, and two 10% EtOAc/$\phi H$ fractions, the third 10% and first 20% EtOAc/$\phi H$ provide the bulk of the product (~1.6 g from 10 ml filtrate) as judged by tlc (20% EtOAc/CHCl$_3$; silica gel GF). Recrystallization from benzene, (1 g in ca. 50 ml concentrated to ~⅓ volume and "spiked" with 1 ml of $H_2O$-saturated benzene): provides 0.24 g 2'; mp (117) 121°–122°. [$\phi H$=benzene.]

Step F

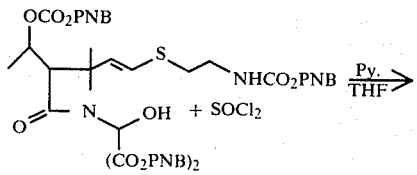

-continued
Step F

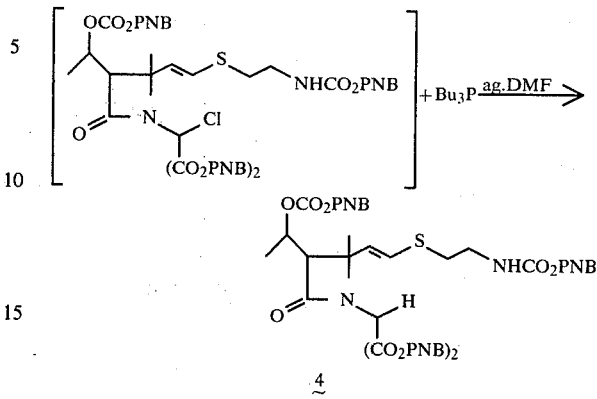

A solution of 1.53 mmole of 3 in $CH_2Cl_2$ is dried over anhydrous $MgSO_4$, filtered, concentrated under a $N_2$ stream, and dried further under high vacuum just prior to the following reaction. To a solution of 3 in 24 ml THF (freshly distilled from LAH) at $-20°$ C. is added 0.206 ml anhydrous pyridine (mw=79; $\rho$=0.982; 2.56 mmole). With stirring under $N_2$, 294 mg of freshly distilled thionyl chloride (mw=119; 2.47 mmole) in 5 ml THF is added dropwise. The reaction mixture is stirred for 10 minutes at $-20°$ C., then ½ hour at 0° C. and finally 1 hour at 25° C. The pyridine hydrochloride is filtered under $N_2$ and washed with 20 ml THF. The filtrate is concentrated under a $N_2$ stream followed by pumping on high vacuum. The resulting foam is swirled in 25 ml anhydrous THF, and a small amount of orange-red insoluble material is filtered off under $N_2$. The filtrate is re-concentrated as above to a foam.

To this freshly prepared chloro compound is added with stirring a freshly shaken suspension of 678 mg tributylphosphine (mw=202; 3.36 mmole) in 36.5 ml 9:1 DMF-$H_2O$ followed by 294 mg $K_2HPO_4$ (mw=174; 1.69 mmole). The reaction mixture is stirred at 25° C., for 35 minutes. After dilution with 120 ml EA and 60 ml brine, the layers are separated, and the aqueous one is extracted two times with EA. The combined organic layers are washed one time with brine, dried over anhydrous $MgSO_4$, filtered and concentrated under a $N_2$ stream followed by pumping on high vacuum to give crude 4.

The material is chromatographed on 100 g silica gel (height=28.5 cm; d=4 cm) packed and applied in $CHCl_3$ and eluted with 0.5% MeOH in $CHCl_3$. Those fractions containing clean product are combined, concentrated under a $N_2$ stream and then on high vacuum to give 4. Contaminated fractions are re-chromatographed on silica gel thin layer plates (eluant=50% acetone/hexane; extraction of desired u.v. band with $CHCl_3$ and EA) to provide additional 4.

Step G

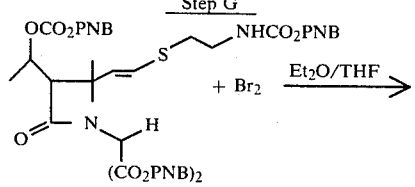

-continued
Step G

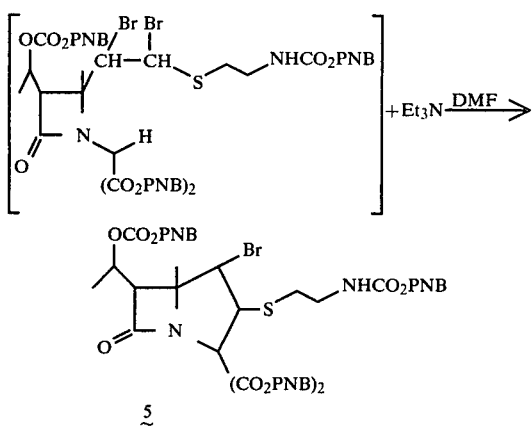

To 8.5 ml pentane (dried over 4A Linde molecular sieves) is added 0.2 ml Br₂ (mw=160; 3.9 mmole). To 0.746 mmole of 4 in 18 ml THF (freshly distilled from LAH) and 5.7 ml Et₂O (dried over 3A 1/16" Linde molecular sieves) at 0° C. under N₂ with stirring is added dropwise 1.8 ml of the above 0.45 M Br₂ solution (0.81 mmole). After 15 minutes at 0° C., 0.42 ml triethylamine (mw=101; ρ=0.729; 3.03 mmole) is added, immediately followed by 10.5 ml ice-cold DMF (distilled from CaSO₄ at 40 mm and stored over 4A Linde molecular sieves). The ice-bath is removed, and stirring at room temperature is continued for 2 hours. The reaction mixture is poured into a stirred, ice-cold mixture of 3.1 1 M KH₂PO₄-70 ml H₂O-100 ml EA. The layers are separated, and the aqueous one is saturated with NaCl and re-extracted with EA. The combined organic layers are washed once with brine, dried over anhydrous MgSO₄, and filtered. The filtrate is concentrated under a N₂ stream and then pumped on high vacuum to give crude 5.

The material is chromatographed on 60 g silica gel (diameter=2.8 cm) packed and applied in CHCl₃ and is eluted with 100 ml-2% EA/CHCl₃; 100 ml-4% EA/CHCl₃ and then 5% EA/CHCl₃ for the remainder of the chromatography. The fractions containing pure 5 are combined, concentrated under a N₂ stream, and pumped on high vacuum to give 5.

Step H

[Structure of compound 5]

-continued
Step H

[Structure of compound 6]

To 29 mg anhydrous silver fluoride (mw=127; 0.23 mmole) is added a solution of 0.14 mmole of 5 in 3.5 ml anhydrous pyridine. The stoppered reaction mixture is stirred at room temperature in the dark for one hour and then poured into 20 ml cold water −30 ml EA. After separation of the layers, the aqueous one is extracted two times with EA and one time with CHCl₃. Each organic layer is extracted one time with H₂O and one time with brine. The combined organic layers are dried over anhydrous MgSO₄, filtered, and concentrated under a N₂ stream followed by pumping on high vacuum to give crude 6.

Preparative thin layer chromatography (eluant=40% acetone/hexane; repeated extraction of desired u.v. band with a large volume of CHCl₃) yields slightly contaminated 6. Re-chromatography on silica using EA in CHCl₃ as an eluting system gives pure 6.

STEP I

[Structure of compound 6]

→

[Structure of compound 7]

A solution of 0.082 mmole of 6 in 0.9 ml S-collidine (distilled from powdered KOH∼30 mm pressure) is added to 13.4 mg anhydrous LiI (dried for few hours at 100° C. over P₂O₅ under vacuum) (mw=134; 0.1 mmole). With stirring under N₂, the reaction mixture is heated in an oil bath in 120° C. After a total of 30 minutes, the reaction mixture is cooled to 25° C., diluted with CH₂Cl₂, and transferred to a round bottom flask for concentration under a N₂ stream and then on high vacuum. Partitioning the residue between EA-H₂O and 1 ml 1 M KH₂PO₄ is followed by extraction of the aqueous layer two additional times with EA and one time with CHCl₃. Each organic layer is then back-washed with brine. The combined organic layers are dried over anhydrous MgSO₄, filtered, concentrated under a N₂ stream and then on high vacuum to give crude 7.

Preparative thin layer chromatography on silica gel (plate is eluted two times with 40% acetone/hexane; repeated extraction of desired u.v. bands with large volume of CHCl₃) yields recovered starting material and the desired product 7.

STEP J

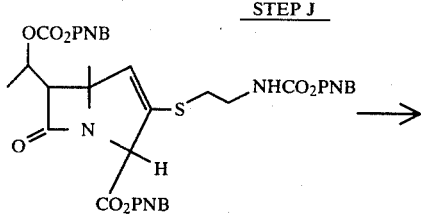

7

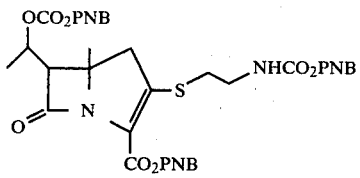

8

To 0.064 mmole of 7 in 0.7 ml DMSO (distilled from CaH₂ at 8 mm and stored over 4A Linde molecular sieves) is added 100 μl diisopropylamine (distilled from NaH under N₂ and stored over 4A Linde molecular sieves) (mw=101; ρ=0.722; 0.71 mmole). The stoppered reaction mixture is stirred for a few minutes and then allowed to stand for 2 hours. The amine and most of the DMSO are then concentrated off under high vacuum with no external heating. The residue is passed quickly through a column of silica gel (packed, applied, and eluted with EA) to remove residual DMSO. After concentration under a N₂ stream of all fractions having u.v. absorbance, the material is chromatographed on a thin layer silica gel plate (eluant=50% EA/CHCl₃; repeated extraction of desired u.v. bands with a large volume of chloroform) to give the pure product 8 and unisomerized 7. Starting material is re-submitted to the reaction conditions and isolation procedure two more times to yield additional 8.

STEP K

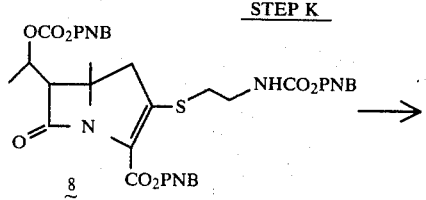

8

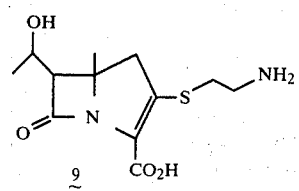

9

To ca.5 mg 8 is added 0.60 ml dioxane, 0.05 ml ethanol, 0.35 ml deionized water and 0.01 ml of 1.0 M K₂HPO₄. To the resultant clear solution is added 5 mg of 10% Pd/C. The suspension is flushed with N₂, then 5-6 times alternately with 50 psi H₂ and vacuum. Finally, it is shaken under a 50 psi H₂ atmosphere for 30-40 min. After centrifugation, the Pd/C is washed and centrifuged 2-3× with 0.5 ml portions of deionized water. The combined centrifugates are extracted 5×1-2 ml ether. Residual ether is removed under vacuum and the aqueous solution applied to an XAD-2 column (20×140 mm). Fractions of 100 drops (6-7 ml) are collected, with continuous UV monitoring, eluting with deionized water. Emergence of strongly UV absorbing material begins around fractions 3-5 and is usually complete by fractions 25-30. Early fractions are examined by UV to exclude those few deemed too strongly absorbing in the 270-280 mμ region. The remaining fractions are combined and lyophilized. The residue is evaluated by dissolving in 10.0 ml of deionized water and measuring the UV absorbtion at 298 mμ.

EXAMPLE 9

Step A

Preparation of 24[1-(t-butyldimethylsilyl)-4-methyl-4-vinyl-2-azetidinone]

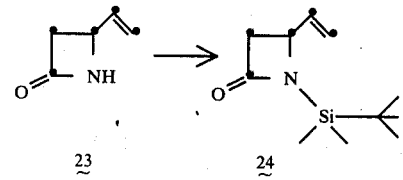

23    24

A solution of 23[4-methyl-4-vinyl-2-azetdinone] (11.89 mmoles) and triethylamine (1.82 ml, 13.08 mmoles) in anhydrous N,N-dimethylformamide is placed under a nitrogen atmosphere, cooled to 0° C. and treated with t-butyldimethylchlorosilane (1.885 g., 12.48 mmoles) resulting in the immediate appearance of a heavy white precipitate. This mixture is stirred for one hour while gradually warming to room temperature. The mixture is partitioned between 30 ml. methylene chloride and 90 ml cold 1 M potassium dihydrogen phosphate. The aqueous phase is extracted with 20 ml methylene chloride. The combined organic phases are washed four times with 30 ml portions of water and finally with 50 ml brine. The methylene chloride solution is dried over anhydrous magnesium sulfate and filtered. The filtrate is evaporated under reduced pressure to give 24[1-(t-butyldimethylsilyl)-4-vinyl-4-methyl-2-azetidinone].

Step B

Preparation of 25[1-(t-butyldimethylsilyl)-3-(1-hydroxyethyl)-4-methyl-4-vinyl-2-azetidinone]

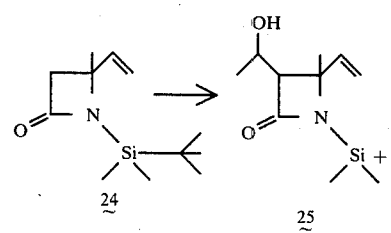

24    25

To a solution of freshly prepared lithium diisopropylamide (7.82 mmoles) in 36 ml anhydrous tetrahydrofuran under a nitrogen atmosphere at −75° C. is added a solution of 24[1-(t-butyldimethylsilyl)-4-vinyl-2-azetidinone] (7.11 mmoles) in 10 ml anhydrous THF. The resulting yellow solution of the lithium enolate is, after 16 minutes, treated with acetaldehyde (1.59 ml, 28.4 mmoles). In 10 minutes, the reaction is quenched by adding 30 ml of a saturated aqueous ammonium chloride solution. This mixture is extracted with 50 ml and 25 ml portions of ethyl acetate. The combined ethyl acetate solutions are washed with 50 ml of brine and dried over anhydrous magnesium sulfate. The drying agent is removed by filtration and the filtrate is evaporated in vacuo to give the crude product as a yellow oil. Purification by chromatography on silica gel eluting with 10% ethyl acetate/chloroform gives 25[1-(t-butyldimethylsilyl)-3-(1-hydroxyethyl)-4-vinyl-4-methyl-2-azetidinone.]

Step C

Preparation of 26[1-(t-butyldimethylsilyl)-3-(1-p-nitrobenzylcarbonyldioxyethyl)-4-methyl-4-vinyl-2-azetidinone]

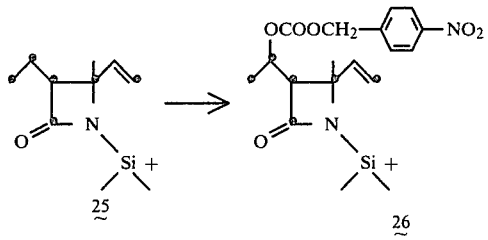

Under nitrogen at −78° C. a solution of 25 (0.220 mmole) in 1 ml of anhydrous tetrahydrofuran is treated with 2.4 M n-butyllithium in hexane (101 μl, 0.242 mmole). To this solution is added, in five minutes, a solution of p-nitrobenzyl chloroformate (52 mg, 0.242 mmole) in anhydrous tetrahydrofuran. After stirring at −78° C. for a period of 55 minutes, 10 ml of a saturated aqueous ammonium chloride solution is added and the product extracted into ethyl acetate. The combined ethyl acetate solutions are washed with brine and dried over anhydrous magnesium sulfate. The drying agent is removed by filtration, and the filtrate is evaporated in vacuo. Purification by preparative thick-layer chromatography on silica gel developing with 5% ethyl acetate/chloroform gives 26.

Step D

Desilylation of 26 to provide 27[3-(1-p-nitrobenzylcarbonyldioxyethyl)-4-methyl-4-vinyl-2-azetidinone]

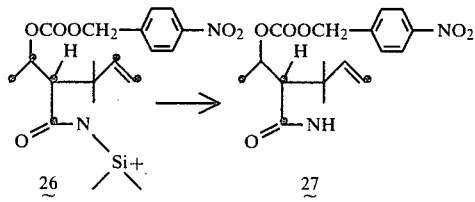

A solution of 26[1-(t-butyldimethylsilyl)-3-(1-p-nitrobenzylcarbonyldioxyethyl)-4-methyl-4-vinyl-2-azetidinone] (0.141 mmole) in 2 ml of 0.5 N HCl/MeOH is stirred at room temperature (25° C.) for a period of 3 hours. The solution is then cooled to 0° C. and neutralized by the addition of 5 ml of 5% aqueous sodium bicarbonate. The product is extracted into ethyl acetate (10 ml, 2×5 ml). The combined ethyl acetate solutions are washed with water (2×5 ml) and 10 ml brine and then dried over anhydrous magnesium sulfate. The drying agent is removed by filtration, and the filtrate is evaporated in vacuo to give an oil. Preparative thick-layer chromatography of this material on silica gel developing with 10% ethyl acetate/chloroform gives 27[3-(1-p-nitrobenzylcarbonyldioxyethyl)-4-methyl-4-vinyl-2-azetidinone].

Step E

Preparation of 14 via 28 by sulfenyl halide addition and dehydrohalogenation

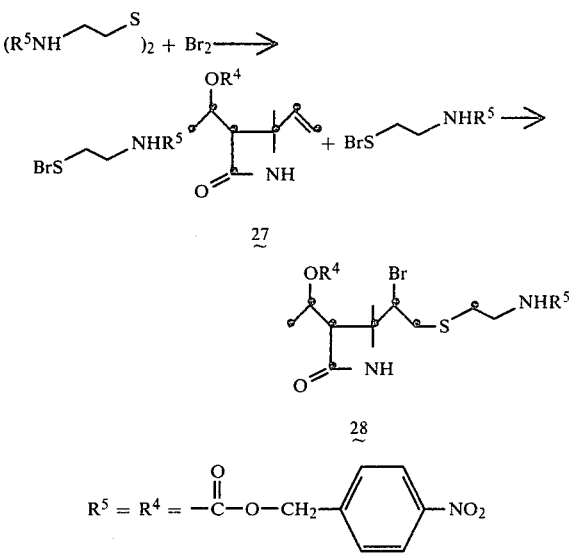

A solution of the N-p-nitroCB$^Z$ cysteamine disulfide, 96 mg (0.19 mmoles) in 1.5 ml THF (freshly distilled from LiAlH$_4$) is cooled to −25° C. and treated dropwise with stirring with 0.5 ml of a solution of 135 mg Br$_2$ in sieve dried CCl$_4$ (2.2 ml final volume; portion added is equivalent to 0.19 mmoles of Br$_2$). The resultant orange solution is stirred at −20° C. for 5 min. then treated with 54.0 mg of the vinyl azetidinone, 27, in 0.5 ml sieve dried CH$_2$Cl$_2$. The color lightens to yellow. The mixture is allowed to come to 0° C. over 5–10 minutes. Examination by tlc (silica 5% MeOH in CH$_2$Cl$_2$ or 20% EtOAc in CH$_2$Cl$_2$) shows a main spot with R$_f$ and Ce$^{IV}$+/H+/heat characteristics different from either disulfide or starting azetidinone. The reaction mixture is concentrated to 0.5 ml under N$_2$, streaked directly on two 8″×8″ 1000μ silica GF plates, and developed with 20% EtOAc in CH$_2$Cl$_2$. The main band under U.V., is scraped off, and extracted with EtOAc to give 28.

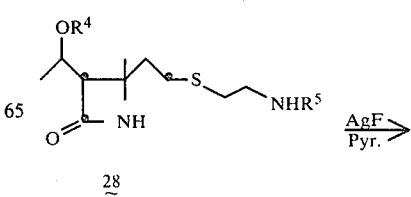

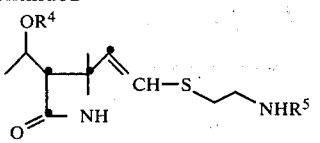

14

Treatment with 1.01 g. AgF(mw=127; 7.95 mmole) of 4.2 mmole of 28 in 34 ml. pyridine at room temperature in the dark under N₂ for 1 hr. is followed by concentration of the entire reaction mixture under high vacuum and with a water bath at 25°-30° C. to a brown-black residue. After chasing a few times with CHCl₃, the residue is slurried in CH₂Cl₂ and run through a short column of silica gel (eluting with 2% MeOH/CH₂Cl₂) thus removing most of the silver salts. The fractions containing product are combined. Chromatography on silica gel (1% MeOH/CH₂Cl₂) provides the desired product 14. Preparative thin layer chromatography on silica gel of column fractions which still contained less polar impurities (2.5% MeOH/CH₂Cl₂), provides additional product.

Step F

Following the exact procedure described in Example 8, Steps D-K, except making the indicated substitutions, species 14 of Example 9, Step E, is converted to I:

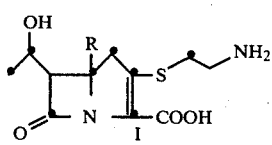

R = CH₃

EXAMPLE 10

Preparation of Bis(p-Nitrobenzyloxycarbonylaminoethyl)disulfide

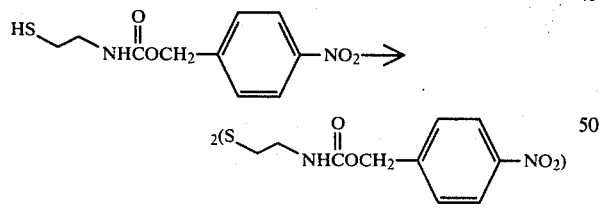

Under nitrogen at −20° C., bromine (1.21 ml, 0.022 mmole) is added to a solution of p-nitrobenzyloxycarbonylaminoethanethiol (11.28 g, 0.044 mole) in 100 ml of anhydrous tetrahydrofuran. The cooling bath is removed, and the cold solution is stirred for 15 minutes. The solution is then diluted with 400 ml ethyl acetate and washed with 200 ml 1 M pH 7 phosphate buffer, 200 ml 1 M dibasic potassium phosphate, water (2×200 ml, 100 ml) and 200 ml brine. It is dried over anhydrous magnesium sulfate and filtered. The filtrate is evaporated in vacuo giving a yellow solid residue. This material is chromatographed on silica gel eluting with 5% ethyl acetate/chloroform to give 10.5 g of crystalline bis(p-nitrobenzyloxycarbonylaminoethyl)disulfide:

| IR (CH₂Cl₂)μ: | 3.04NH |
| | 5.96 carbonyl |
| | 6.22, 6.61 nitro |
| NMR (CDCl₃) δ: | 8.24⎫ |
| | 7.54⎭ d, J = 8.5Hz, ArH |
| | 5.37, broad s, NH |
| | 5.26, s, ArCH₂O |
| | 3.60, q, J = 6Hz and 6Hz, NHCH₂CH₂ |
| | 2.86, t, J = 6Hz, NHCH₂CH₂S |

EXAMPLE 11

Following the procedure of the foregoing Examples and text except substituting the appropriately substituted acyloxybutadiene for the illustrated methyl substituted acyloxybutadiene starting material, there is obtained the following representative species of the present invention.

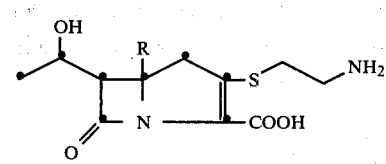

For every entry in Table I, the butadiene reagent is given by the general formula:

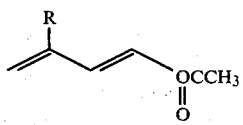

wherein R is defined in Table I.

TABLE I

| Compound | R | Reagents, Remarks |
|---|---|---|
| 1. | CH₂CH₃ | |
| 2. | —CH₂—furyl | |
| 3. | isopropyl | |
| 4. | cyclopropyl | |
| 5. | propyl | |
| 6. | phenyl | |
| 7. | tolyl | R; R = o, m & p - methyl |
| 8. | cyclobutyl | |
| 9. | cyclopentyl | |
| 10. | cyclohexyl | |
| 11. | CH₂-cyclohexyl | |
| 12. | 4-methylcyclohexyl | —CH₃ |
| 13. | —CH₂—cyclopropyl | |

TABLE I-continued

| Compound | R | Reagents, Remarks |
|---|---|---|
| 14. | ⌬—R; R = o, m & p - Cl, Br, F, —OCH$_3$, | |
| 15. | (cyclopentylmethyl) | |
| 16. | (cyclopropylethyl) | |
| 17. | (cyclopropylmethyl) | |
| 18. | —CF$_3$ | |
| 19. | (propyl zigzag) | |
| 20. | (butyl zigzag) | |

EXAMPLE 12

Preparation of Pharmaceutical Compositions

One such unit dosage form consists in mixing 120 mg of I:

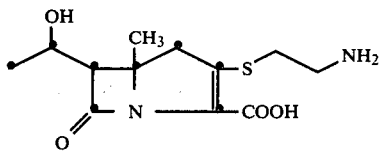

with 20 mg of lactose and 5 mg of magnesium stearate and placing the 145 mg mixture into a No. 3 gelatin capsule. Similarly, by employing more of the active ingredient and less lactose, other dosage forms can be put up in No. 3 gelatin capsules and should it be necessary to mix more than 145 mg of ingredients together, larger capsules such as compressed tablets and pills can also be prepared. The following examples are illustrative of the preparation of pharmaceutical formulations:

| TABLET | PER TABLET |
|---|---|
| I | 125 mg. |
| Cornstarch, U.S.P. | 6 mg. |
| Dicalcium Phosphate | 192 mg. |
| Lactose, U.S.P. | 190 mg. |
| Magnesium Stearate | Balance/800 mg. |

The active ingredient is blended with the dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and magnesium stearate is added and the mixture is compressed into tablets, approximately 0.5 inch in diameter each weighing 800 mg.

| | PER TABLET |
|---|---|
| PARENTERAL SOLUTION | |
| Ampoule: | |
| I | 500 mg. |
| Diluent: Sterile water for injection | 2 cc. |
| OPTHALMIC SOLUTION | |
| I | 100 mg. |
| Hydroxypropylmethyl cellulose | 5 mg. |
| Sterile water | to 1 ml. |
| OTIC SOLUTION | |
| I | 100 mg. |
| Benzalkonium chloride | 0.1 mg. |
| Sterile water | to 1 ml. |
| TOPICAL OINTMENT | |
| I | 100 mg. |
| Polyethylene Glycol 4000 U.S.P. | 400 mg. |
| Polyethylene Glycol 400 U.S.P. | 1.0 gram. |

What is claimed is:

1. A compound of the structure

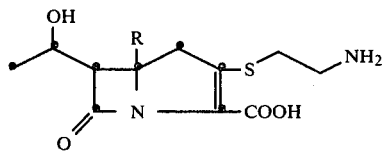

and the pharmaceutically acceptable salts thereof; wherein R is a member selected from the group consisting of loweralkyl, cycloloweralkyl, cycloloweralkyl-loweralkyl, benzyl, phenyl, chlorophenyl, bromophenyl, fluorophenyl, methoxyphenyl, loweralkylphenyl and trifluoromethyl.

2. A compound according to claim 1 wherein R is a member selected from the group consisting of methyl, ethyl, isopropyl, phenyl, p-methylphenyl, benzyl, cyclopropyl, cyclobutyl, cyclopentyl, cyclohexyl and trifluoromethyl.

3. An antibiotic pharmaceutical composition comprising a therapeutically effective amount of a compound according to claim 1 and a pharmaceutical carrier therefor.

4. A compound having the structure:

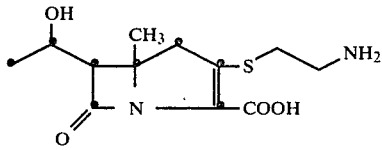

and its pharmaceutically acceptable salts.

* * * * *